United States Patent
Seo et al.

(10) Patent No.: US 9,465,969 B2
(45) Date of Patent: Oct. 11, 2016

(54) METHOD FOR PROVIDING QR CODE-BASED SERVICE FOR CHECKING FOR OCCURRENCE OF COCKTAIL EFFECT OF DRUGS USING SMART DEVICE

(71) Applicants: Woong Jin Seo, Wonju (KR); You Young Jang, Wonju (KR)

(72) Inventors: Woong Jin Seo, Wonju (KR); You Young Jang, Wonju (KR)

(*) Notice: Subject to any disclaimer, the term of this patent is extended or adjusted under 35 U.S.C. 154(b) by 0 days.

(21) Appl. No.: 14/910,029

(22) PCT Filed: Jul. 24, 2014

(86) PCT No.: PCT/KR2014/006772
§ 371 (c)(1),
(2) Date: Feb. 4, 2016

(87) PCT Pub. No.: WO2015/020334
PCT Pub. Date: Feb. 12, 2015

(65) Prior Publication Data
US 2016/0180131 A1 Jun. 23, 2016

(30) Foreign Application Priority Data
Aug. 8, 2013 (KR) .................. 10-2013-0094162

(51) Int. Cl.
*G06F 17/00* (2006.01)
*G06K 7/10* (2006.01)

(52) U.S. Cl.
CPC ................. *G06K 7/10861* (2013.01)

(58) Field of Classification Search
USPC .......................................................... 235/375
See application file for complete search history.

(56) References Cited

U.S. PATENT DOCUMENTS

2011/0093279 A1* 4/2011 Levine .................. G06F 19/326
705/2

FOREIGN PATENT DOCUMENTS

| JP | 2002207826 A | 7/2002 |
| JP | 2010158478 A | 7/2010 |
| KR | 1019980071912 A | 10/1998 |
| KR | 1020020090775 A | 12/2002 |

OTHER PUBLICATIONS

International Search Report for PCT/KR2014/006772 mailed Oct. 14, 2014.

* cited by examiner

*Primary Examiner* — Jamara Franklin
(74) *Attorney, Agent, or Firm* — STIP Law Group, LLC

(57) ABSTRACT

The present invention suggests a method for providing a QR code-based service for checking whether or not a cocktail effect of drugs will occur using a smart device, which enables even an ordinary person with no specialist expertise to easily check whether or not a cocktail effect will occur when taking a plurality of drugs and to refrain from administration of a drug which may result in a negative effect, and thus, can prevent the abuse of drugs, by extracting drug information by scanning a QR code provided on the package of the drug to be taken, which a user intends to take, by means of a smart device, determining, using administration information previously registered in a database, whether or not the drug being taken and the drug to be taken cause a cocktail effect due to an interaction caused thereby, and outputting the determination result.

3 Claims, 6 Drawing Sheets

METHOD FOR PROVIDING QR CODE-BASED SERVICE FOR CHECKING FOR OCCURRENCE OF COCKTAIL EFFECT OF DRUGS USING SMART DEVICE

CROSS-REFERENCE TO RELATED APPLICATIONS

This application is the U.S. National Phase under 35 U.S.C. §371 of International Application No. PCT/KR2014/006772 filed on Jul. 24, 2014, which in turn claims the benefit of Korean Application No. 10-2013-0094162, filed on Aug. 8, 2013, the disclosures of which are incorporated by reference into the present application.

TECHNICAL FIELD

The present invention generally relates to a method for providing a service for checking whether or not a cocktail effect occurs. More particularly, the present invention relates to a method for providing a QR code-based service for checking whether or not a cocktail effect of drugs occurs using a smart device.

BACKGROUND ART

A drug is a chemical for the treatment of a disease. As the kinds of drug, there are not only prescription drugs, the use of which is restricted to the case of prescription of a doctor, but also non-prescription drugs, which a patient can buy directly from a pharmacist after consultation. Also, quasi-drugs, which can be bought in drugstores or supermarkets without any specific limitation, can also be considered drugs.

Recently, as quasi-drugs, which include household drugs, have come to be sold in convenience stores and the like, there is growing concern over drug abuse and misuse. That is, even if a drug can be bought without restriction, because a user may abuse or misuse the drugs, it is necessary to handle this problem.

In particular, when mixtures of different drugs are used, a "cocktail effect", which refers to the interaction of one drug with another drug, may occur. In special cases, a cocktail effect may induce positive effects. For example, specialists use a cocktail therapy for the treatment of AIDS. However, because a cocktail effect may result in negative effects in many cases, great care is needed.

If a patient has multiple diseases, a mixture of drugs that causes serious side effects may be prescribed due to the complex interactions between the diseases and the patient, even though the drugs are prescribed by a doctor. Also, a cocktail effect may occur because multiple drugs are used as a result of the patient's carelessness. However, unlike specialists, patients have difficulty in predicting a cocktail effect arising from the use of a mixture of drugs. Therefore, there is an urgent need to develop a method that enables an ordinary person to determine whether a cocktail effect is likely to occur and to refrain from taking a drug that may cause negative effects.

Meanwhile, a QR code is a two-dimensional grid matrix type code, 'QR' being an acronym of 'Quick Response'. A conventional one-dimensional barcode can store 20 bytes of numeric information, more or less, while a QR code can store a maximum of 7089 numeric characters, a maximum of 4296 ASCII characters, a maximum of 2953 bytes of binary data (each byte comprising 8 bits), or a maximum of 1817 characters of Kanji. Also, a QR code has a high recognition speed and a high recognition rate, and is superior in the accuracy of data restoration. Furthermore, because users may easily acquire information stored in a QR code by scanning the QR code using a smart device, no additional device for recognizing the QR code is necessary, and the extent of utilization of QR codes has increased with the rapid spread of smart devices. Accordingly, various methods have been developed in order to make use of QR codes, but QR codes have not been used in the field of drugs.

DISCLOSURE

Technical Problem

Accordingly, the present invention has been made keeping in mind the above problems, and an object of the present invention is to provide a method for providing a QR code-based service for checking whether or not a cocktail effect of drugs occurs using a smart device. The method extracts information about a drug to be taken by scanning a QR code provided on the package of the corresponding drug using a smart device, determines whether a cocktail effect may be caused by the interaction between the drug to be taken and a drug currently being taken using drug administration information stored in advance in a database, and outputs a determination result, whereby an ordinary person without expertise may easily check whether a cocktail effect will occur when taking multiple drugs, and may refrain from taking drugs that may have negative effects, thus preventing drug abuse or misuse.

Technical Solution

In order to accomplish the above object, a method for providing a QR code-based service for checking whether or not a cocktail effect of drugs occurs using a smart device according to an aspect of the present invention may include:

by the smart device that is capable of scanning a QR code, (1) registering information about a drug that is being taken by a user as drug administration information in a database;

(2) extracting information about a drug to be taken by scanning a QR code on a package of the drug;

(3) determining whether or not a cocktail effect occurs when the drug that is being taken and the drug to be taken are taken simultaneously, using the registered drug administration information and the extracted information about the drug to be taken; and (4) outputting a result of the determination in (3) to an output unit.

Desirably, the drug administration information may include information about a drug that is being taken by a family member of the user.

Desirably, the drug administration information or the information about the drug to be taken may include information about a cocktail effect related to the drug that is being taken or a cocktail effect related to the drug to be taken.

Desirably, the method may further include (a) storing, by the smart device, information about drugs that cause a cocktail effect when the drugs are simultaneously taken and information about the cocktail effect in the database, before (2).

More desirably, in (a), the information about the drugs and the information about the cocktail effect may be updated at a preset time interval or when an update signal is received.

Desirably, after (1) and before (3), the method may further include, by the smart device, selecting a drug being taken for which a determination of whether the cocktail effect occurs due to the drug is required from the drug administration information registered in (1), and receiving the selection, wherein in (3), whether or not a cocktail effect occurs may be determined using drug administration information about the selected drug and the information about the drug to be taken, which is extracted in (2).

Desirably, in the smart device, an application for implementing (1) to (4) may be installed.

<Description of the Reference Numerals in the Drawings>

100: QR code  100: smart device
200: server
S10: Store information about drugs that cause cocktail effect and information about cocktail effect in database
S100: Register drug administration information in database
S200: Extract information about drug by scanning QR code
S250: Receive selection of drug being taken for which determination of whether cocktail effect can occur is required
S300: Determine whether cocktail effect can occur
S400: Output determination result to output unit Advantageous Effects According to the method for providing a QR code-based service for checking whether a cocktail effect of drugs occurs using a smart device proposed by the present invention, information about a drug to be taken is extracted by scanning a QR code provided on the package of the corresponding drug using a smart device, whether a cocktail effect may be caused by the interaction between the drug to be taken and a drug being taken is determined using drug administration information stored in advance in a database, and the determination result is output, whereby an ordinary person without expertise may easily check whether a cocktail effect will occur when taking multiple drugs, and may refrain from taking a drug that may have negative effects, thus preventing drug abuse and misuse.

BEST MODE

Figure 1:
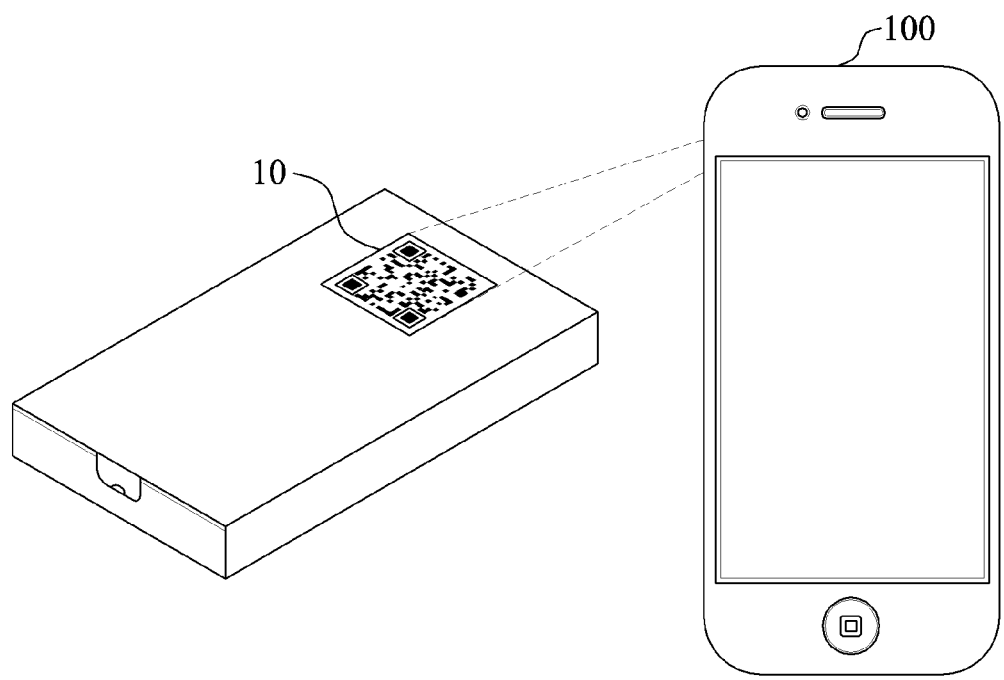
FIG. 1 is a view illustrating the configuration of a system for implementing a method for providing a QR code-based service for checking whether a cocktail effect of drugs occurs using a smart device according to an embodiment of the present invention.

Hereinafter, embodiments of the present invention are described with reference to the accompanying drawings in order to describe the present invention in detail so that those having ordinary knowledge in the technical field to which the present invention pertains can easily practice the present invention. In the following description of the present invention, detailed descriptions of known functions and configurations which are deemed to make the gist of the present invention obscure will be omitted. It should be noted that the same reference numerals are used to designate the same or similar elements throughout the drawings.

In the following description of the present invention, it will be understood that when an element is referred to as being "connected" or "coupled" to another element, it can be directly connected or coupled to the other element, or intervening elements may be present. Also, it will be further understood that the terms "comprises," "comprising,", "includes" and/or "including", when used herein, specify the presence of stated elements, but do not preclude the presence or addition of one or more other elements, unless the context clearly indicates otherwise.

FIG. 1 is a view illustrating the configuration of a system for implementing a method for providing a service based on a QR code 10 for checking whether or not a cocktail effect of drugs occurs using a smart device 100 according to an embodiment of the present invention. As illustrated in FIG. 1, the method for providing a service based on a QR code 10 for checking whether or not a cocktail effect of drugs occurs using a smart device 100 according to an embodiment of the present invention may be implemented using the smart device 100. More specifically, the method may be implemented by scanning the QR code 10 printed on the package of a drug using the smart device 100.

In other words, the present invention provides a QR code 10 that stores information about a drug by printing or affixing the QR code 10 on the package of the corresponding drug, whereby a smart device 100 may extract the information about the drug by scanning the QR code 10. That is, information about a drug to be taken may be extracted by scanning the QR code 10 provided on the package of the corresponding drug using the smart device 100, whether a cocktail effect can be caused by the interaction between the drug to be taken and the drug currently being taken by a user may be determined using drug administration information, which is the information about the drugs being taken by the user that has been stored in advance in a database, and the result of the determination may be output.

Of course, depending on the embodiment, information about the ingredients of a product may be stored in a Radio Frequency Identification (RFID) tag, a Near Field Communication (NFC) tag, or the like, rather than a QR code 10. However, a QR code 10 may be printed on or attached to a drug package at low cost, and may be easily and quickly recognized using a commonly used smart device 100 without an additional device.

The smart device 100 is capable of scanning a QR code 10, and may be a user terminal that implements a method for providing a service based on a QR code 10 for checking whether or not a cocktail effect of drugs occurs using a smart device 100 according to an embodiment of the present invention. The smart device 100 is a product that is almost unlimited as to the functions thereof. In other words, many functions may be modified or extended through applications. The smart device 100 may be a smart phone, a smart pad, a table PC, a smart camera, a smart TV, or the like. However, the smart device 100 of the present invention is not limited to the above-mentioned types of terminals, but if a terminal can extract information about a drug from a QR code 10 by scanning the QR code 10 and determine whether or not a cocktail effect occurs using the drug administration information registered in the database, the terminal may be used as the smart device 100 of the present invention, regardless of the type of the terminal.

In particular, an application for implementing a method for providing a service based on a QR code 10 for checking whether or not a cocktail effect of drugs occurs using a smart device 100 according to an embodiment of the present invention may be installed in the smart device 100 of the present invention. When the application installed in the smart device 100 is executed, various interfaces that facilitate registering user's drug administration information, scanning a QR code 10, and easily checking the result of the determination of whether or not a cocktail effect will occur may be provided.

Figure 2:
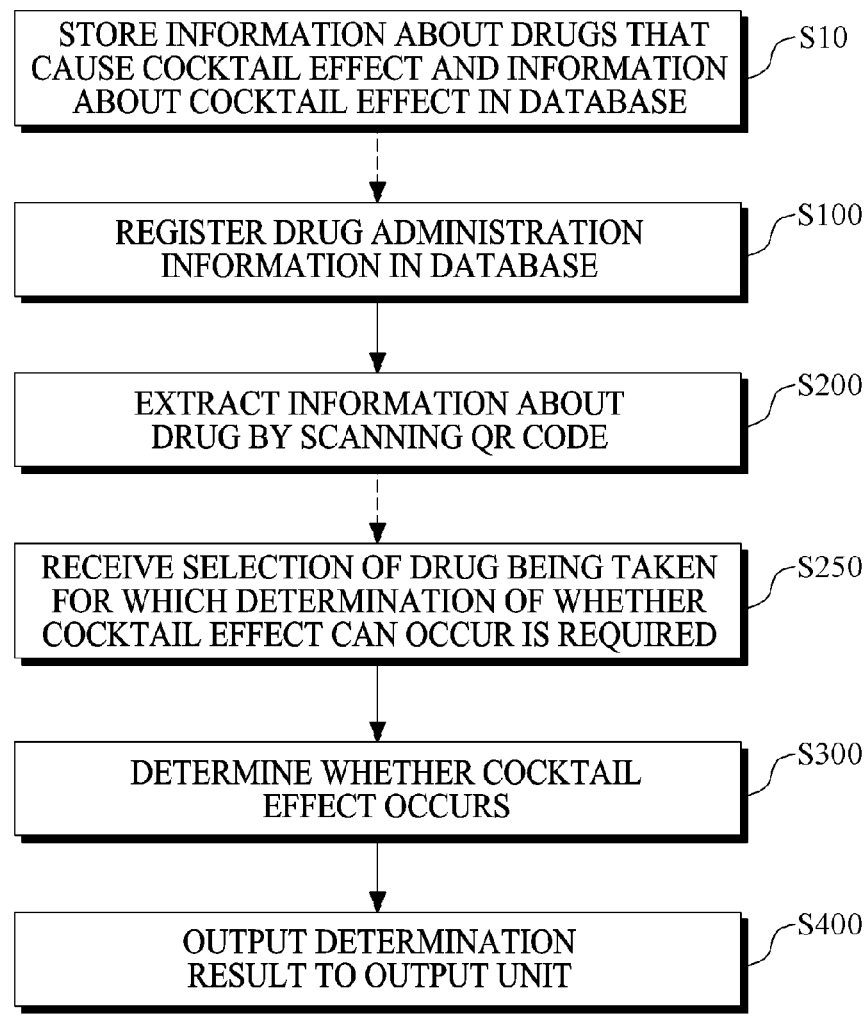
FIG. 2 is a view illustrating the flow of a method for providing a QR code-based service for checking whether a cocktail effect of drugs occurs using a smart device according to an embodiment of the present invention.

FIG. 2 is a view illustrating the flow of a method for providing a service based on a QR code 10 for checking whether or not a cocktail effect of drugs occurs using a smart device 100 according to an embodiment of the present invention. As illustrated in FIG. 2, the method for providing a service based on a QR code 10 for checking whether or not a cocktail effect of drugs occurs using a smart device 100 according to an embodiment of the present invention may include registering drug administration information in a database (S100), extracting information about a drug by scanning a QR code 10 (S200), determining whether or not a cocktail effect can occur (S300), and outputting the result of the determination to an output unit (S400). The method may further include storing information about drugs that cause a cocktail effect and information about the cocktail effect in the database (S10) and selecting the drug, for which a determination of whether or not a cocktail effect will occur is necessary, from among the drugs being taken and receiving the selection (S250).

At step S10, the smart device 100 may store information about drugs that cause a cocktail effect when the drugs are taken simultaneously and information about the cocktail effect in the database. In other words, the smart device 100 may store information about a cocktail effect that may occur when two or more drugs are simultaneously taken in the database. Here, the drugs that cause a cocktail effect may be stored in the form of a table or an index. In this case, with regard to a specific drug, the table is referred to or the index is searched for a drug that may cause a cocktail effect when the drug is used along with the specific drug.

Meanwhile, at step S10, the information about drugs or the information about the cocktail effect may be updated at a preset time interval or when an update signal is received. In other words, the latest information may be maintained by updating the existing information using information about new drugs and newly discovered cocktail effects.

Figure 3:
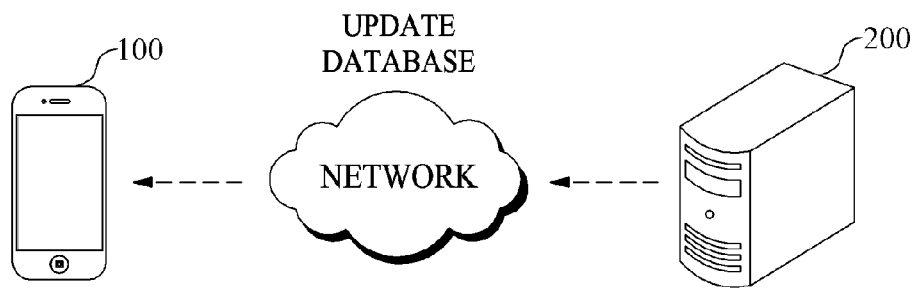
FIG. 3 is a view illustrating the process for updating a database in a method for providing a QR code-based service for checking whether a cocktail effect of drugs occurs using a smart device according to an embodiment of the present invention.

FIG. 3 is a view illustrating the process for updating a database in a method for providing a service based on a QR code 10 for checking whether or not a cocktail effect of drugs occurs using a smart device 100 according to an embodiment of the present invention. As illustrated in FIG. 3, at step S10 of the method for providing a service based on a QR code 10 for checking whether or not a cocktail effect of drugs occurs using a smart device 100 according to an embodiment of the present invention, the smart device 100 may receive update information from a server 200 and update the database. Here, the smart device 100 may update the database through a network that includes the Internet, an intranet, wired and wireless communication networks, mobile communication networks, and the like. Particularly, if there is information about a cocktail effect that is required to be updated, the server 200 transmits an update signal to the smart device 100 so as to enable the smart device 100 to update the information.

At step S100, the smart device 100 may register drug administration information, which is information about drugs that a user is taking, in the database. Specifically, the drug administration information may be information about the drugs that are currently being taken by the user, and may further include information about drugs being taken by the family members of the user. In other words, because not only the user's drug administration information but also the family members' drug administration information is registered in the database, cocktail effects may also be determined and managed for the drugs being taken by the user's family members.

Meanwhile, the drug administration information may include information about a cocktail effect related to the drug being taken. In other words, in order to input the drug administration information, drug names may be input, but various pieces of information about the drugs, such as a cocktail effect or the like, may also be additionally input. Also, the smart device 100 may receive the drug administration information by registering information about the drug being taken, extracted from the QR code 10 on the package of the drug, by scanning it using the smart device 100.

Meanwhile, according to an embodiment, step S10 may be performed after step S100, whereby the information about the drug being taken by the user, information about a drug that causes a cocktail effect when the drug is taken along with the drug currently being taken by the user, and information about the cocktail effect may be stored in the database. Because the database of the smart device 100 may have a limited storage capacity, only information about the cocktail effect related to the drug being taken by the user is stored, rather than storing information about cocktail effects of all kinds of drugs, whereby the database may be used more effectively.

Figure 4:
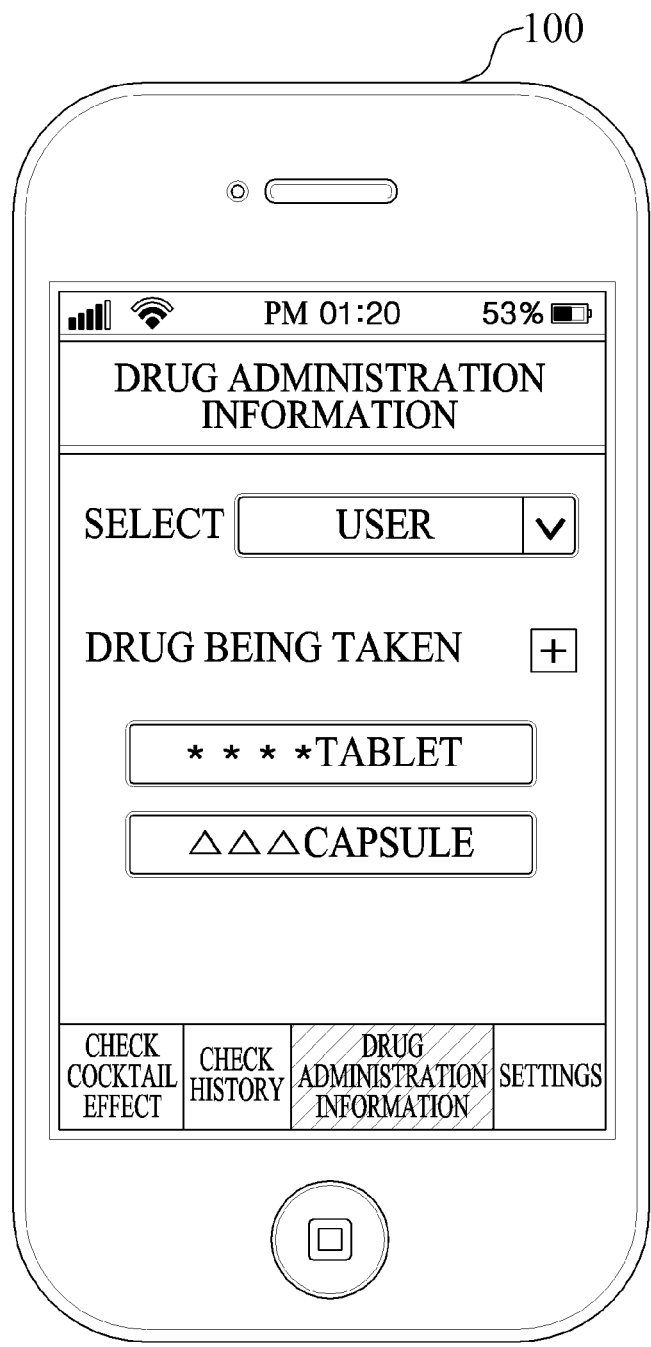
FIG. 4 is a view illustrating an example in which a smart device receives drug administration information in a method for providing a QR code-based service for checking whether a cocktail effect of drugs occurs using a smart device according to an embodiment of the present invention.

FIG. 4 is a view illustrating an example in which a smart device 100 receives drug administration information in a method for providing a service based on a QR code 10 for checking whether or not a cocktail effect of drugs occurs using a smart device 100 according to an embodiment of the present invention. As illustrated in FIG. 4, at step S100 of the method for providing a service based on a QR code 10 for checking whether or not a cocktail effect of drugs occurs using a smart device 100 according to an embodiment of the present invention, the names of drugs that are being taken may be input. Here, a user or a user's family member, who is taking a drug, may be registered, and then the drugs being taken may be input and managed for each of the user, the user's spouse, the user's children, and so on.

At step S200, the smart device 100 may extract information about the drug to be taken by scanning the QR code 10 provided on the package of the corresponding drug. As illustrated in FIG. 1, a QR code 10 may be provided on the package of a drug, and the QR code 10 may store information about the drug, which includes the ingredients of the drug, the dose of the drug, and the like. At step S200, the information about the drug may be extracted from the QR code 10 by scanning the QR code 10 using the camera module installed in the smart device 100. Here, the information about the drug may further include information about a cocktail effect, in addition to the ingredients and the dose of the drug. That is, information about a drug that is restricted to be taken along with the drug that is planned to be taken and information about symptoms that can be caused when the corresponding drug is taken along with the drug that is planned to be taken may be further included.

Figure 5:
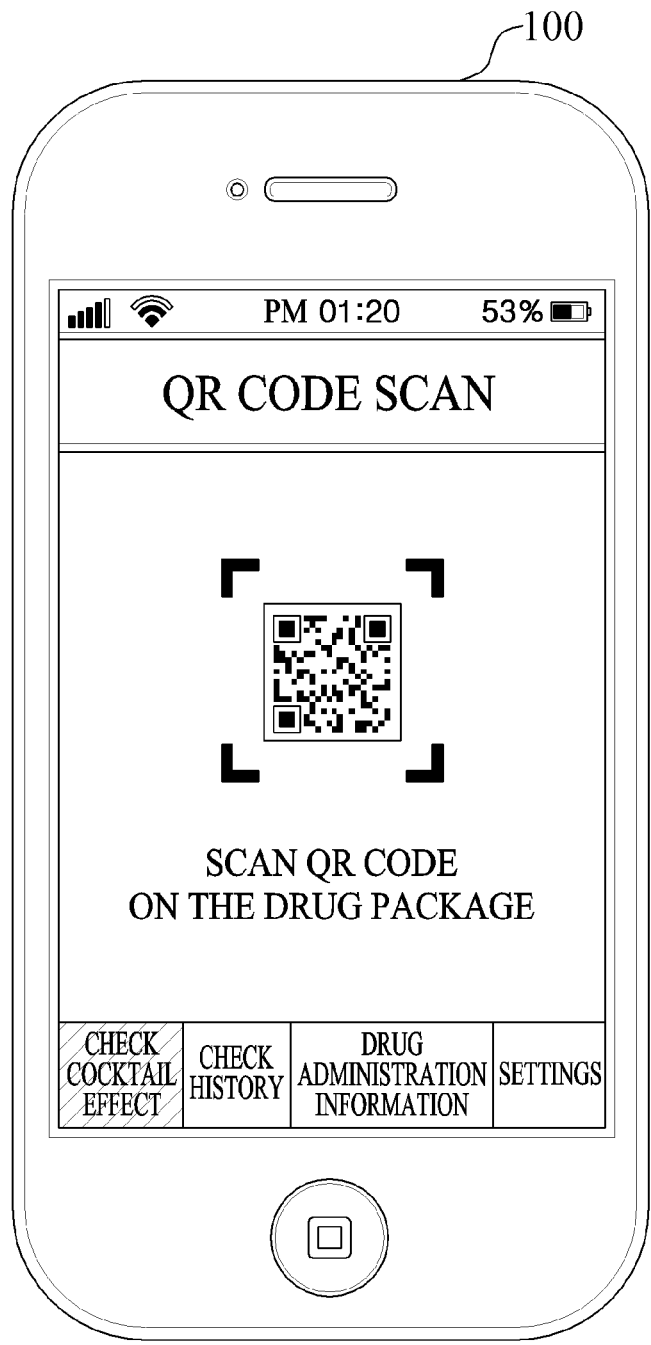
FIG. 5 is a view illustrating an example in which a smart device scans a QR code in a method for providing a QR code-based service for checking whether a cocktail effect of drugs occurs using a smart device according to an embodiment of the present invention.

FIG. 5 is a view illustrating an example in which a smart device 100 scans a QR code 10 in a method for providing a service based on a QR code 10 for checking whether or not a cocktail effect of drugs occurs using a smart device 100 according to an embodiment of the present invention. As illustrated in FIG. 5, at step S200 of the method for providing a service based on a QR code 10 for checking whether or not a cocktail effect of drugs occurs using a smart device 100 according to an embodiment of the present invention, a QR code 10 may be scanned by executing an application installed in the smart device 100. The information about the drug, extracted by scanning the QR code 10 at step S200, may be stored in the database, whereby the user may check the information again by selecting a "check history" menu item.

At step S250, a drug for which a determination of whether or not a cocktail effect will occur is required is selected from the drug administration information registered at step S100, and the smart device 100 may receive the selection. The drug administration information registered at step S100 may include information about multiple drugs that are being taken, and the multiple drugs may include a drug that is not to be taken simultaneously with the drug that is planned to be taken. Therefore, at step S250, the smart device 100 receives the selection of a drug for which a determination of whether or not a cocktail effect can occur is required because the drug will be taken simultaneously with the drug that is planned to be taken. Also, if the drug administration information is registered for each family member, the family member who will take the corresponding drug may be selected.

Figure 6:
FIG. 6 is a view illustrating an example in which drugs being taken are selected using a smart device in a method for providing a QR code-based service for checking whether a cocktail effect of drugs occurs using a smart device according to an embodiment of the present invention.

FIG. 6 is a view illustrating an example in which a smart device 100 is used to select a drug being taken in a method for providing a service based on a QR code 10 for checking whether or not a cocktail effect of drugs occurs using a smart device 100 according to an embodiment of the present invention. As illustrated in FIG. 6, at step S250 of the method for providing a service based on a QR code 10 for checking whether or not a cocktail effect of drugs occurs using a smart device 100 according to an embodiment of the present invention, a drug to be checked for the occurrence of a cocktail effect when taken along with the drug that is planned to be taken may be selected from the list of the drugs that have been registered as the drugs being taken. Because the information about the drug to be taken is acquired by scanning the QR code 10 at step S200, whether the cocktail effect will occur may be determined using information about the drug selected at step S250. As illustrated in FIG. 6, the drug selected at step S250 may comprise multiple drugs.

At step S300, it may be determined whether or not a cocktail effect will occur when the drug being taken and the drug to be taken are taken simultaneously using the drug administration information registered by the smart device 100 and the drug information extracted by the smart device 100. In this case, whether a cocktail effect will occur may be determined at step S300 using the information about a drug, extracted at step S200, and the information about the drug selected from the drug administration information at step S250.

Whether a cocktail effect will occur may be determined using the information stored at step S10. Also, if a QR code 10 includes information about a drug that may cause a cocktail effect, that is, information about a drug that should not be taken simultaneously with the corresponding drug and information about symptoms when the drug is taken simultaneously with the corresponding drug, whether a drug to be taken causes a cocktail effect may be checked using the information about the drug extracted from the QR code 10.

At step S400, the smart device 100 may output the determination result of step S300 to an output unit. Here, the output unit may be a display unit of the smart device 100, a speaker of the smart device 100, a haptic actuator of the smart device 100, or the like. That is, the determination result of step S300 may be delivered to a user through various methods using the sense of vision, hearing, touch, and the like, and multiple methods may be used together for outputting the results.

Figure 7:
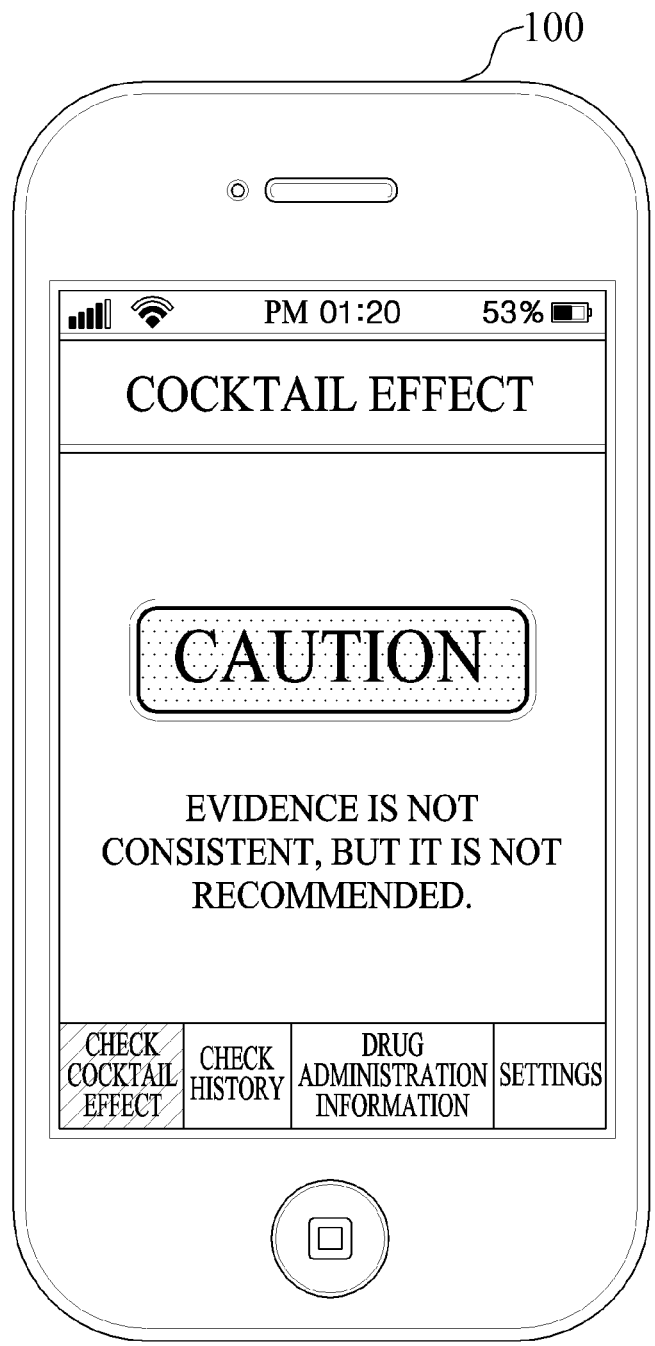
FIG. 7 is a view illustrating an example in which a smart device outputs a determination result in a method for providing a QR code-based service for checking whether a cocktail effect of drugs occurs using a smart device according to an embodiment of the present invention.

FIG. 7 is a view illustrating an example in which a smart device 100 outputs a determination result in a method for providing a service based on a QR code 10 for checking whether or not a cocktail effect of drugs occurs using a smart device 100 according to an embodiment of the present invention. As illustrated in FIG. 7, at step S400 of the method for providing a service based on a QR code 10 for checking whether or not a cocktail effect of drugs occurs using a smart device 100 according to an embodiment of the present invention, the result of step S300, that is, the result of determination of whether a cocktail effect can occur, may be output to the display unit of the smart device 100. Here, depending on whether the cocktail effect can occur, the determination result may be output as "safe", "caution", "danger", or the like. If the determination result is "caution" or "danger", information about symptoms that may be caused by the cocktail effect may be displayed along with the determination result.

Although the preferred embodiment of the present invention has been disclosed for illustrative purposes, those skilled in the art will appreciate that various modifications, additions and substitutions are possible, without departing from the scope and spirit of the invention as disclosed in the accompanying claims.

The invention claimed is:

1. A method for providing a QR code-based service for checking whether or not a cocktail effect of drugs occurs using a smart device, comprising:

by the smart device that is capable of scanning a QR code, (1) registering information about a drug that is being taken by a user as drug administration information in a database and storing information about a first drug that causes a cocktail effect when taken simultaneously with the drug that is being taken and information about the cocktail effect in the database, wherein the information about the first drug is stored in a form of a table or an index and wherein the information about the first drug and the information about the cocktail effect are updated at a predetermined time interval or when an update signal is received;

(2) extracting information about a drug to be taken by scanning a QR code on a package of the drug to be taken;

(3) determining whether or not a cocktail effect occurs when the drug that is being taken and the drug to be taken are taken simultaneously, using the registered drug administration information for the drug that is being taken and the extracted information about the drug to be taken, wherein the determining step (3) is performed using a search result of the table or the index, (4) outputting a result of the determination in (3) to an output unit; and, after (1) and before (3), further comprising a step of selecting by using the smart device the drug that is being taken, for which a determination of whether the cocktail effect occurs due to the drug is required, from the drug administration information registered in the step (1) and receiving the selection, wherein the smart device includes the database, an application implementing the steps (1) to (4), and interfaces that register user's drug administration information in the database, scan a QR code, and check a result of the determination of whether or not a cocktail effect will occur.

2. The method of claim 1, wherein the drug administration information further includes information about a drug that is being taken by a family member of the user.

3. The method of claim 1, wherein the drug administration information or the information about the drug to be taken includes information about a cocktail effect related to the drug that is being taken or a cocktail effect related to the drug to be taken.

* * * * *